United States Patent
Abe et al.

(10) Patent No.: US 7,270,683 B2
(45) Date of Patent: Sep. 18, 2007

(54) HAIRDYE COMPOSITION

(75) Inventors: Hideyuki Abe, Tokyo (JP); Akira Kawamata, Wakayama (JP); Akira Kiyomine, Tokyo (JP)

(73) Assignee: Kao Corporation, Tokyo (JP)

( * ) Notice: Subject to any disclaimer, the term of this patent is extended or adjusted under 35 U.S.C. 154(b) by 336 days.

(21) Appl. No.: 10/510,712

(22) PCT Filed: Apr. 18, 2002

(86) PCT No.: PCT/JP02/03869

§ 371 (c)(1),
(2), (4) Date: Apr. 21, 2005

(87) PCT Pub. No.: WO03/086336

PCT Pub. Date: Oct. 23, 2003

(65) Prior Publication Data

US 2005/0172419 A1    Aug. 11, 2005

(51) Int. Cl.
*A61K 7/13*     (2006.01)
(52) U.S. Cl. .................. 8/405; 8/406; 8/431; 8/602; 540/475; 540/554
(58) Field of Classification Search ............ 8/405, 8/406, 431, 602; 540/475, 554
See application file for complete search history.

(56) References Cited

U.S. PATENT DOCUMENTS 6,540,791 B1 *   4/2003   Dias ........................ 8/111

FOREIGN PATENT DOCUMENTS

| EP | 458397 | 11/1991 |
|---|---|---|
| JP | 2000-144188 | 5/2000 |
| WO | WO95/30733 | 11/1995 |
| WO | WO96/01311 | 1/1996 |
| WO | 97 24106 | 7/1997 |
| WO | 97 24107 | 7/1997 |

OTHER PUBLICATIONS

STIC Search Report dated Apr. 4, 2007.*

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Provided is a hair dye composition to be used as a mixture of a first part containing an alkali agent and a second part containing an oxidizing agent, wherein the composition comprises (a) a triazacyclononane compound (1) or salt thereof, (b) 0.1 to 12 wt. %, in terms of hydrogen peroxide, of an oxidizing agent, and (c) 0.05 to 10 wt. % of an alkali agent, and the mixture has a pH of from 7.5 to 12.

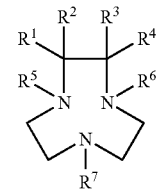

(1)

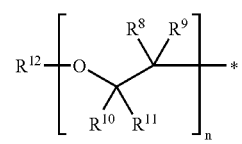

(2)

($R^1$ to $R^4$: H or $C_{1-6}$ alkyl which may be substituted by OH, $R^5$ to $R^7$: H, (substituted) $C_{1-6}$ alkyl, (substituted) aralkyl, (substituted) heteroarylalkyl, (substituted) aryl, (substituted) heteroaryl, (substituted) $C_{1-6}$ acyl, or a group (2) (in which $R^8$ to $R^{12}$ represents H, $C_{1-6}$ alkyl, aralkyl or aryl and n stands for 2 to 30).

The hair dye composition of the present invention has excellent hair bleaching power, can dye the hair into a bright favorable color tone, and moreover has less hair damage and less scalp irritation.

2 Claims, No Drawings

HAIRDYE COMPOSITION

TECHNICAL FIELD

The present invention relates to hair dye compositions causing less damage to the hair and less irritation to the scalp upon or after their application and having excellent bleaching or dyeing power.

BACKGROUND ART

For hair dyeing, two-part type permanent hair dyes composed of a first part containing an alkali agent and a second part containing an oxidizing agent have been used popularly. The oxidizing agent of the second part is added in order to impart a bright color tone to the hair by enhancing the hair dyeing effect through the coupling reaction of an oxidation dye intermediate and at the same time accelerating oxidation and decomposition of melanin granules in the hair. The alkali agent of the first part is, on the other hand, incorporated in order to enhance the hair dyeing effect and activate the action of the oxidizing agent to enhance the bleaching effect. For Bleaching or dyeing of the hair into a brighter color tone compared with the original color tone of the hair, sufficient bleaching power is necessary. Hair bleaching power however usually depends on the amounts of alkali and oxidizing agents, so that they must be added in large enough amounts when the hair dye is used for such a purpose.

Conventional hair dyes contain ammonia or organic amines as the alkali agent and hydrogen peroxide as the oxidizing agent. Addition of them in large amounts is however accompanied with the drawback that it is apt to damage the hair or irritate the scalp in proportion to the amount used.

DISCLOSURE OF THE INVENTION

An object of the present invention is to provide a hair dye composition having excellent bleaching power, capable of dying the hair into a bright favorable color tone, and in addition, causing less damage to the hair and less irritation to the scalp.

The present inventors have found that the above-described object can be attained by incorporating a specific triazacyclononane compound in a hair dye. A complex of a triazacyclononane compound with a heavy metal, especially with manganese, is known as a bleaching catalyst for clothes. Addition of such a complex to a hair dye is described in U.S. Pat. No. 6,004,355. The investigation by the present inventors, however, has revealed that the addition of such a complex to a hair bleaching agent or a hair dye deteriorates the hair bleaching effect. In the present invention, excellent hair bleaching or dyeing power can be attained by the use of the below-described triazacyclononane compound singly, not as a complex with a heavy metal.

In the present invention, there is thus provided a hair dye composition to be used as a mixture of a first part containing an alkali agent and a second part containing an oxidizing agent, wherein the composition comprises the following components (a) to (c):

(a) a triazacyclononane compound represented by the following formula (1):

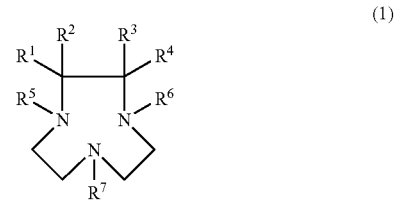

(wherein, $R^1$, $R^2$, $R^3$ and $R^4$ each represents a hydrogen atom or a $C_{1-6}$ alkyl group which may be substituted by a hydroxy group, $R^5$, $R^6$ and $R^7$ each represents a hydrogen atom, a $C_{1-6}$ alkyl group which may have a substituent, an aralkyl group which may have a substituent, a heteroarylalkyl group which may have a substituent, an aryl group which may have a substituent, a heteroaryl group which may have a substituent, a $C_{1-6}$ acyl group which may have a substituent or a group represented by the following formula (2):

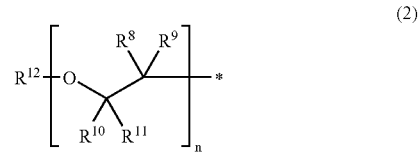

(in which $R^8$, $R^9$, $R^{10}$, $R^{11}$ and $R^{12}$ each represents a hydrogen atom, a $C_{1-6}$ alkyl group, an aralkyl group or an aryl group, and n stands for 2 to 30), or salt thereof;

(b) 0.1 to 12 wt. %, in terms of hydrogen peroxide, of an oxidizing agent, and (c) 0.05 to 10 wt. % of an alkali agent; and the mixture has a pH of from 7.5 to 12.

When the above-described conditions are satisfied, the alkali agent and oxidizing agent can be made to work efficiently in the hair, leading to an improvement in the hair bleaching or dyeing power. Accordingly, it is possible to reduce the amounts of alkali agent and oxidizing agent without deteriorating the hair bleaching or dyeing power and to reduce the hair damage and scalp irritation. In other words, when the alkali agent and oxidizing agent are used in amounts equal to the conventional ones, hair bleaching or dyeing power can be improved without boosting the hair damage and scalp irritation.

BEST MODE FOR CARRYING OUT THE INVENTION

In the formula (1), examples of the $C_{1-6}$ alkyl group represented by $R^1$, $R^2$, $R^3$ or $R^4$ include methyl, ethyl, propyl, butyl, pentyl, hexyl, isopropyl, isobutyl and isopentyl groups. Of these, $C_{1-3}$ alkyl groups are preferred. Examples of these groups substituted by a hydroxy group include hydroxymethyl, 2-hydroxyethyl, 2-hydroxypropyl and 3-hydroxypropyl groups. $R^1$, $R^2$, $R^3$ and $R^4$ may be the same or different.

Examples of the groups represented by $R^5$, $R^6$ or $R^7$ in formula (1) are the following. The $C_{1-6}$ alkyl groups include methyl, ethyl, propyl, butyl, pentyl, hexyl, isopropyl, isobutyl and isopentyl groups. Of these, $C_{1-3}$ alkyl groups are preferred. The aralkyl groups include benzyl, 2-phenylethyl, 1-phenylethyl and 3-phenylpropyl groups. The heteroarylalkyl groups include 2'-pyridylmethyl and 2-(2'-pyridyl)ethyl groups. The aryl groups include phenyl, 1-naphthyl and 2-naphthyl groups. The heteroaryl groups include 2-pyridyl, 3-pyridyl and 4-pyridyl groups. The acyl groups include acetyl, propionyl, butanoyl, pentanoyl and hexanoyl groups.

Examples of the substituent for these groups include hydroxy group, $C_{1-6}$ alkoxy groups, $C_{1-6}$ acyl groups, carboxy group, sulfo group, phosphono group, sulfoxy group, phosphonoxy group, $C_{1-6}$ alkoxycarbonyl groups, aminocarbonyl group which may have, on the nitrogen atom thereof, one or two $C_{1-6}$ alkyl groups or hydroxy groups as a substituent, amino group which may be substituted by one or two $C_{1-6}$ alkyl groups, mercapto group, dialkylphosphino groups, diarylphosphino groups, fluorine atom, chlorine atom, bromine atom and iodine atom. Two or more of these groups or atoms may be substituted for the above-described groups.

In the substituent (2) represented by $R^5$, $R^6$ or $R^7$, the $C_{1-6}$ alkyl group, aralkyl group and aryl group represented by $R^8$, $R^9$, $R^{10}$, $R^{11}$ or $R^{12}$ are similar to those described above. $R^5$, $R^6$ and $R^7$ may be the same or different.

Examples of the salt of the triazacyclononane derivative (1) include salts of an inorganic acid or an organic acid such as hydrochloric acid, sulfuric acid, phosphoric acid, acetic acid, propionic acid, lactic acid, citric acid, succinic acid, hydrobromic acid, hydroiodic acid, methanesulfonic acid or perchloric acid. The triazacyclononane compound (1) in which a group represented by $R^5$, $R^6$ and/or $R^7$ has one or more substituents such as carboxy, sulfoxy, phosphono, sulfoxy or phosphonoxy group which will be an anion can also be used as a salt such as sodium salt, potassium salt, ammonium salt or alkanolammonium salt.

Triazacyclononane compounds (1) are known compounds. Triazacyclononane compounds having, on the nitrogen atom thereof, no substituent, that is, those having a hydrogen atom as each of $R^5$, $R^6$ and $R^7$ can be prepared in a process as described in, for example, Japanese Patent No. 2788550. By using these triazacyclononane compounds as a starting substance and adopting a process as described, for example, in J. Chem. Soc. Dalton. Trans. 83-90(1993), Japanese Patent No. 3107550 or Japanese Patent No. 3107547, triazacyclononane compounds having, on one, two or all of the three nitrogen atoms thereof, a substituent can be prepared. Triazacyclononane compounds having, on the nitrogen atoms thereof, two or three substituents which are different from each other are available by using a triazacyclononane having a substituent on each of 1 or 2 nitrogen atoms as a starting material and in addition, another reaction reagent.

The followings are specific examples of the triazacyclononane compounds (1) used in the present invention.

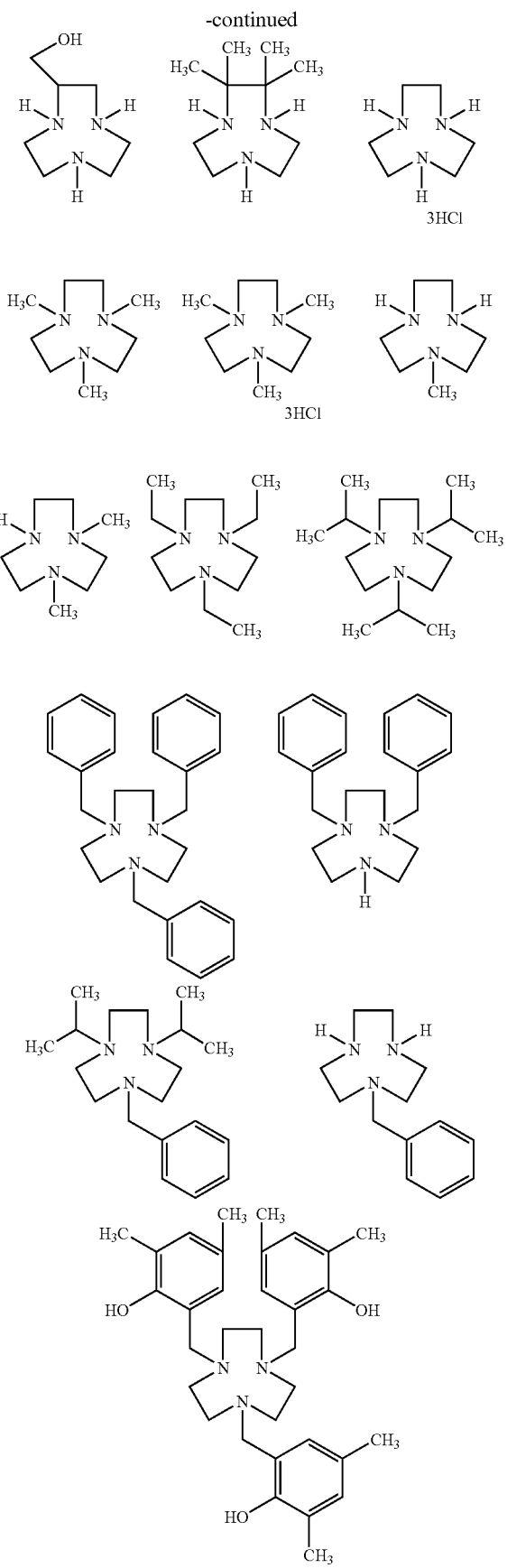

-continued
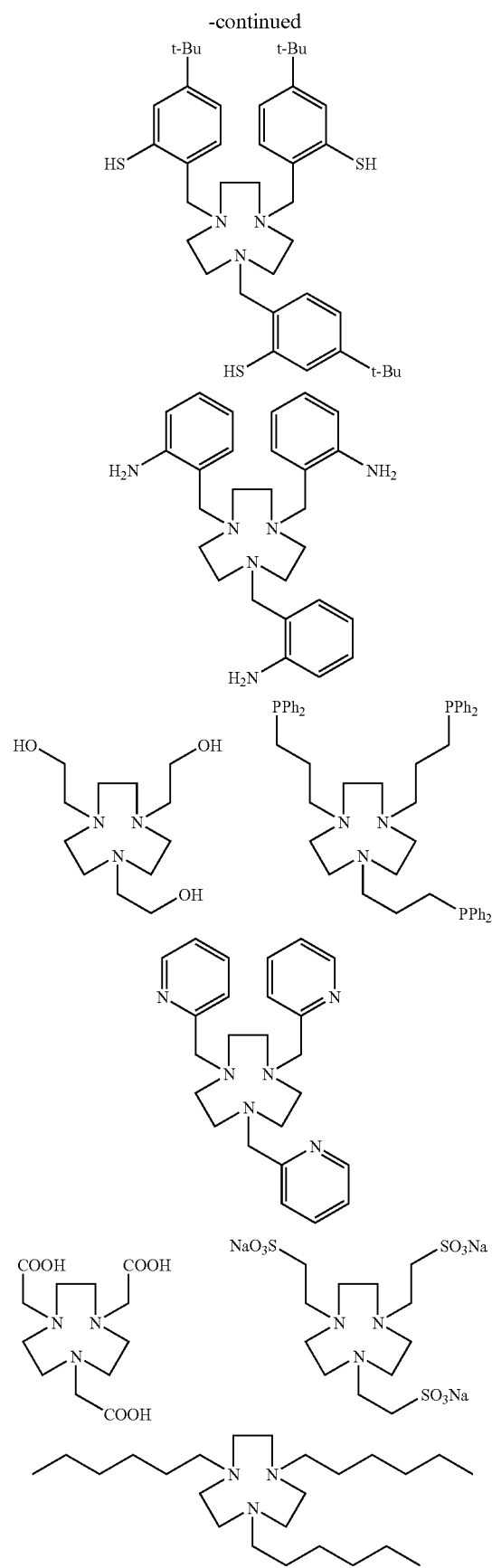
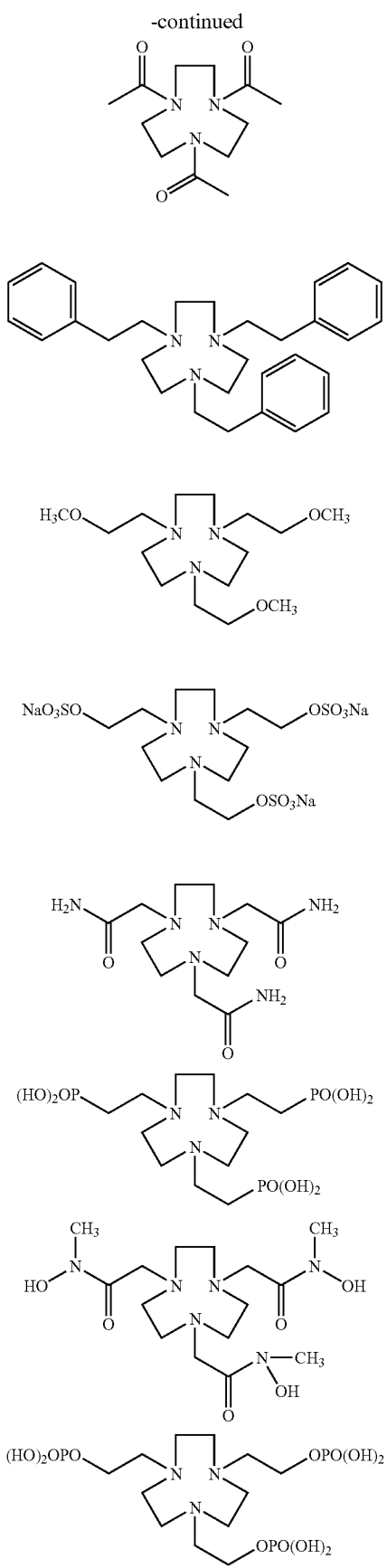

-continued

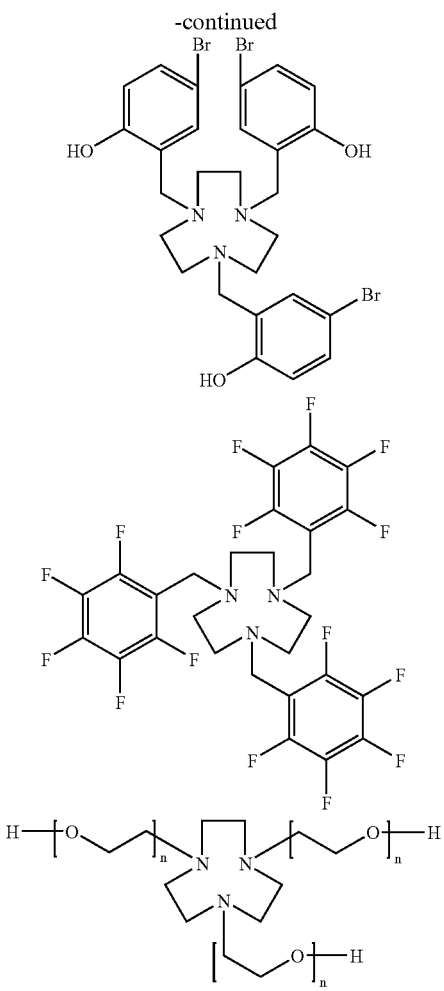

The average of n = 5.

The above-described triazacyclononane compounds (1) or salts thereof can be used singly or in combination as Component (a). In order to attain sufficient hair bleaching and hair dyeing effect, the content of component (a) is preferably from 0.01 to 20 wt. %, more preferably from 0.02 to 10 wt. %, still more preferably from 0.05 to 8 wt. %, yet still more preferably from 0.1 to 5 wt. % in the total composition having the first and second parts.

Examples of the oxidizing agent as Component (b) include hydrogen peroxide and hydrogen peroxide generating agents such as urea peroxide, melamine peroxide, sodium perborate, potassium perborate, sodium percarbonate, and potassium carbonate. Of these, hydrogen peroxide is more preferred. The content of the oxidizing agent in terms of an amount of hydrogen peroxide is from 0.1 to 12 wt. %, preferably from 0.5 to 9 wt. %, more preferably from 1 to 6 wt. % in the total composition of the first and second parts in order to attain sufficient hair bleaching or dyeing effect and reduce hair damage and scalp irritation.

Examples of the alkali agent as Component (c) include ammonia; alkanolamines such as monoethanolamine, isopropanolamine, 2-amino-2-methylpropanol, and 2-aminobutanol; alkanediamines such as 1,3-diaminopropane; and carbonates such as ammonium carbonate, ammonium hydrogen carbonate, guanidine carbonate, sodium carbonate, potassium carbonate, sodium bicarbonate and potassium bicarbonate. Of these, ammonia and alkanolamines are preferred. Monoethanolamine is more preferred as the alkanolamine. At least one of these alkali agents can be used. From the viewpoints of sufficient hair bleaching or dyeing effect and reduction in the hair damage and scalp irritation, the content of these alkali agents ranges from 0.05 to 10 wt. %, preferably from 0.1 to 5 wt. %, more preferably from 0.2 to 3 wt. % in the total composition of the first and second parts. The hair dye composition of the present invention brings about sufficient hair bleaching or dyeing effect without using ammonia as the alkali agent. In this case, it does not cause discomfort during application which will otherwise occur owing to the emission of an offensive odor from ammonia.

In the hair dye composition of the present invention, the first part containing an alkali agent and the second part containing an oxidizing agent are preferably mixed at a first part:second part ratio (weight ratio) falling within a range of from 1:0.5 to 1:3 from the viewpoint of suitability for practical use.

The first part preferably has a pH of from 8 to 12 and the second part preferably has a pH of from 2 to 5, each at 25° C. The hair dye composition after the first and second parts are mixed has a pH of from 7.5 to 12. In consideration of the hair bleaching or dyeing effect and reduction in the skin irritation, the mixture has preferably a pH of from 8 to 11.

Examples of the pH regulator other than the alkali agent as Component (c) include inorganic acids such as hydrochloric acid and phosphoric acid, organic acids such as citric acid, glycolic acid and lactic acid, hydrochlorides such as ammonium chloride and monoethanolamine hydrochloride, and phosphates such as monopotassium dihydrogen phosphate and disodium monohydrogen phosphate.

It is preferred to incorporate as Component (d), in the hair dye composition of the present invention, at least one of ethylenediaminetetraacetic acid, ethylenediaminehydroxyethyltriacetic acid and diethylenetriaminepentaacetic acid, and salts thereof which are known as a chelating agent to be added to hair dye compositions on account of their effect to promote efficient action of the oxidizing agent and alkali agent in the hair. In consideration of the sufficient hair bleaching or dyeing effect, the content of the chelating agent preferably ranges from 0.01 to 5 wt. % of the total composition made of the first and second parts. The chelating agent may be added to one or both of the first and second parts.

The hair dye compositions of the present invention use water and/or an organic solvent as a medium. Examples of the organic solvent include lower alkanols such as ethanol and 2-propanol; aromatic alcohols such as benzyl alcohol and benzyloxyethanol; polyols such as propylene glycol, 1,3-butanediol, diethylene glycol and glycerin; cellosolves such as ethyl cellosolve, butyl cellosolve and benzyl cellosolve, and carbitols such as ethyl carbitol and butyl carbitol.

When the hair dye composition of the present invention is used only for the purpose of hair bleaching, it is used as a hair bleach without containing an oxidation dye intermediate or a direct dye, while when it is used for the purpose of dyeing the hair, it further contains an oxidation dye intermediate or a direct dye.

As such an oxidation dye intermediate, known developers and couplers ordinarily employed for hair dyes can be used. Examples of the developer include p-phenylenediamine, toluene-2,5-diamine, 2-chloro-p-phenylenediamine, N-methoxyethyl-p-phenylenediamine, N,N-bis(2-hydroxyethyl)-p-phenylenediamine, 2-(2-hydroxyethyl)-p-phenylenediamine, 2,6-dimethyl-p-phenylenediamine, 4,4'-diaminodiphenylamine, 1,3-bis(N-(2-hydroxyethyl)-N-(4- aminophenyl)amino)-2-propanol, PEG-3,2,2'-p-phenylenediamine, p-aminophenol, p-methylaminophenol, 3-methyl-4-aminophenol, 2-aminomethyl-4-aminophenol, 2-(2-hydroxyethylaminomethyl)-4-aminophenol, o-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, and 4,5-diamino-1-hydroxyethylpyrazole and salts thereof.

Examples of the coupler include m-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy) propane, m-aminophenol, 2-methyl-5-aminophenol, 2-methyl-5-(2-hydroxyethylamino) phenol, 2,4-dichloro-3-aminophenol, 2-chloro-3-amino-6-methylphenol, 2-methyl-4-chloro-5-aminophenol, N-cyclopentyl-m-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

At least one of the above-exemplified developers and couplers can be used, respectively. The content of each of them is preferably from 0.01 to 5 wt. %, more preferably from 0.1 to 4 wt. % in the total composition of the first part and the second part.

As the direct dye, known acid dyes, basic dyes, disperse dyes and reactive dyes usable for a hair dye can be employed. The acid dyes include, for example, Acid Red 27 (C.I. 16185), Acid Red 51 (C.I.45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Red 92 (C.I. 45410), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685) and Brilliant Black 1 (C.I. 28440).

The basic dyes include, for example, Basic Blue 7 (C.I. 42595), Basic blue 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Yellow 28 (C.I. 48054), Basic Yellow 57 (C.I. 12719), Basic Yellow 87 and Basic Black 2 (C.I. 11825), basic dyes, as described in Japanese Patent Publication No. Sho 58-2204 and Japanese Patent Application Laid-Open No. Hei 9-118832, which contain, in the side chain of the aromatic ring thereof, a quaternized nitrogen atom, and basic dyes, as described in Japanese-Language Laid-Open Publication (PCT) No. Hei 10-502946 and Japanese Patent Applications Laid-Open Nos. Hei 10-182379 and Hei 11-349457.

The direct dyes other than acid dyes and basic dyes include, for example, 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitro-p-hydroxyethylaminophenol, 2-nitro-p-phenylenediamine, 4-nitro-o-phenylenediamine, 4-nitro-m-phenylenediamine, 6-nitro-o-toluidine, 6-nitro-p-toluidine, hydroxyethyl-2-nitro-p-toluidine, N,N'-bis(2-hydroxyethyl)-2-nitro-p-phenylenediamine, 2-chloro-5-nitro-N-hydroxyethyl-p-phenylenediamine, 2-nitro-5-glycerylmethylaniline, 3-methylamino-4-nitrophenoxyethanol, N-ethyl-3-nitro PABA, picramic acid, 2-hydroxyethylpicramic acid, 4-nitrophenylaminoethylurea, Violet No. 201 (C.I.60725), Solvent Yellow 44 (C.I.56200), Disperse Red 17 (C.I.11210), Disperse Violet 1 (C.I.61100), Disperse Violet 4 (C.I.61105), Disperse Blue 3 (C.I.61505), Disperse Blue 7 (C.I.62500), HC Blue No. 2, HC Blue No. 8, HC Orange No. 1, HC Orange No. 2, HC Red No. 1, HC Red No. 3, HC Red No. 7, HC Red No. 8, HC Red No. 10, HC Red No. 11, HC Red No. 13, HC Red No. 16, HC Violet No. 2, HC Yellow No. 2, HC Yellow No. 5, HC Yellow No. 6, HC Yellow No. 7, HC Yellow No. 9, and HC Yellow No. 12.

As the direct dye, the above-exemplified ones may be used singly or in combination, and the content preferably falls within a range of from 0.001 to 5 wt. %, more preferably from 0.01 to 4 wt. %, each based on the whole composition having the first and second parts. The direct dye may be used in combination with the oxidation dye.

To the hair dye composition of the present invention, other components ordinarily employed as raw materials for cosmetics can be added further. Examples of such optional components include hydrocarbons, animal or vegetable oils or fats, higher fatty acids, penetration enhancers, cationic surfactants, natural or synthetic polymers, higher alcohols, ethers, amphoteric surfactants, nonionic surfactants, protein derivatives, amino acids, antiseptics, chelating agents, stabilizers, antioxidants, vegetable extracts, crude drug extracts, vitamins, colorants, perfumes and ultraviolet absorbers.

Similar to oxidation type hair bleaches or hair dyes which have been used popularly at present, the hair dye composition according to the present invention is provided as a two-part composition made of a first part containing an alkali agent and a second part containing an oxidizing agent. The first part and the second part can be used in the form of, for example, liquid, emulsion, cream, gel, paste or mousse. They can also take an aerosol form. The viscosity of the mixture of the first and second parts is preferably such that the resulting mixture will not drop when applied to the hair.

The viscosity of the mixture preferably ranges from 2000 to 100000 mPa·s as measured by a Brookfield rotary viscometer at 25° C.

The bleaching or dyeing of the hair by using the hair dye composition of the present invention may be performed, for example, by mixing the first part and second part of the hair dye composition of the present invention, applying the mixture to the hair at from 15 to 45° C., washing the hair after causing it to act on the hair for from 1 to 60 minutes, preferably from 3 to 45 minutes, and then drying the hair.

EXAMPLES

The followings are compounds used in the below-described Examples.

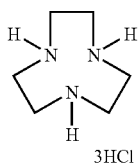

Compound (1a)

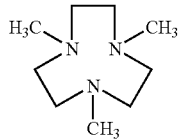

Compound (1b)

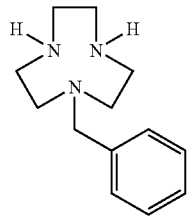

Compound (1c)

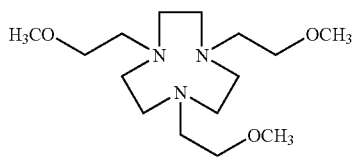

Compound (1d)

Examples 1 to 10

In the conventional manner, oxidation-type hair bleaches as shown in Tables 1 and 2 were prepared.

TABLE 1

(wt. %)

| | | Examples | | | | |
|---|---|---|---|---|---|---|
| | | 1 | 2 | 3 | 4 | 5 |
| First part | Compound (1a) | 0.1 | 2 | | | |
| | Compound (1b) | | | 1 | | |
| | Compound (1c) | | | | 1 | |
| | Compound (1d) | | | | | 1 |
| | 28 wt. % Aqueous ammonia | 6 | | 6 | 3 | |
| | Monoethanolamine | | 5 | | 3 | 5 |
| | Propylene glycol | 10 | 10 | 2 | 2 | 2 |
| | Ethanol | 15 | 15 | | | |

TABLE 1-continued (wt. %)

| | | Examples | | | | |
|---|---|---|---|---|---|---|
| | | 1 | 2 | 3 | 4 | 5 |
| | Polyoxyethylene (20) octyl dodecyl ether | 10 | 10 | | | |
| | Polyoxyethylene (40) cetyl ether | | | 2 | 2 | 2 |
| | Polyoxyethylene (2) cetyl ether | | | 2.5 | 2.5 | 2.5 |
| | Oleic acid diethanolamide | 8 | 8 | | | |
| | Oleyl alcohol | 2 | 2 | | | |
| | Stearyl trimethylammonium chloride | | | 1.5 | 1.5 | 1.5 |
| | Cetanol | | | 1 | 1 | 1 |
| | Liquid paraffin | | | 0.5 | 0.5 | 0.5 |
| | Ammonium chloride | Amount to adjust pH to 9.8 | | | | |
| | Purified water | Balance | | | | |
| Second part | Hydrogen peroxide | 6 | 3 | 3 | 6 | 9 |
| | Methylparaben | 0.1 | 0.1 | 0.1 | 0.1 | 0.1 |
| | Phosphoric acid | Amount to adjust pH to 3.5 | | | | |
| | Purified water | Balance | | | | |

With 1 part by weight of the first part, 1 part by weight of the second part is mixed.

TABLE 2

(wt. %)

| | Examples | | | | |
|---|---|---|---|---|---|
| | 6 | 7 | 8 | 9 | 10 |
| First part | | | | | |
| Compound (1a) | 0.1 | 2 | | | |
| Compound (1b) | | | 1 | | |
| Compound (1c) | | | | 1 | |
| Compound (1d) | 0.1 | | | | 1 |
| Tetrasodium ethylenediaminetetraacetate tetrahydrate | | 1 | 0.5 | | |
| Trisodium ethylenediaminehydroxyethyltriacetate | | | | 2 | |
| Pentasodium diethylenetriaminepentaacetate | | | | | 1 |
| 28 wt. % Aqueous ammonia | 6 | | 6 | 3 | |
| Monoethanolamine | | 5 | | 3 | 5 |
| Propylene glycol | 10 | 10 | 2 | 2 | 2 |
| Ethanol | 15 | 15 | | | |
| Polyoxyethylene (20) octyl dodecyl ether | 10 | 10 | | | |
| Polyoxyethylene (40) cetyl ether | | | 2 | 2 | 2 |
| Polyoxyethylene (2) cetyl ether | | | 2.5 | 2.5 | 2.5 |
| Oleic acid diethanolamide | 8 | 8 | | | |
| Oleyl alcohol | 2 | 2 | | | |
| Stearyl trimethylammonium chloride | | | 1.5 | 1.5 | 1.5 |
| Cetanol | | | 1 | 1 | 1 |
| Liquid paraffin | | | 0.5 | 0.5 | 0.5 |
| Ammonium chloride | Amount to adjust pH to 9.8 | | | | |
| Purified water | Balance | | | | |
| Second part | | | | | |
| Hydrogen peroxide | 6 | 3 | 3 | 6 | 9 |
| Methylparaben | 0.1 | 0.1 | 0.1 | 0.1 | 0.1 |
| Phosphoric acid | Amount to adjust pH to 3.5 | | | | |
| Purified water | Balance | | | | |

With 1 part by weight of the first part, 1 part by weight of the second part is mixed.

After 1 part by weight of the first part was mixed with 1 part by weight of the second part, the mixture was applied to black hair at 30° C. The mixture was allowed to act on the hair for 30 minutes. Then, the hair was shampooed with an ordinary shampoo and dried. As a result of the observation of the color tone of the hair thus bleached, the hair dye compositions each exhibited good bleaching property.

Examples 11 to 18

In the conventional manner, oxidation hair dyes as shown in Tables 3 and 4 were prepared.

TABLE 3

| | Examples (wt. %) | | | |
|---|---|---|---|---|
| | 11 | 12 | 13 | 14 |
| First part | | | | |
| Compound (1a) | 0.1 | | | |
| Compound (2a) | | 1 | | |
| Compound (3a) | | | 1 | |
| Compound (4a) | 0.1 | | | 1 |
| Tetrasodium ethylenediaminetetraacetate tetrahydrate | | 0.5 | | |
| Trisodium ethylenediaminehydroxyethyltriacetate | | | 2 | |
| Pentasodium diethylenetriaminepentaacetate | | | | 1 |
| Toluene-2,5-diamine | 1.9 | 1.9 | 1 | |
| p-Aminophenol | | | | 1 |
| Resorcin | 2 | 2 | | |
| p-Amino-o-cresol | | | | 1.1 |
| 2,4-Diaminophenoxyethanol | | | 1.37 | |
| 28 wt. % Aqueous ammonia | 5 | 5 | 5 | 5 |
| Monoethanolamine | 2 | 2 | 2 | 2 |
| Propylene glycol | 8 | 8 | 8 | 8 |
| Polyoxyethylene (20) isostearyl ether | 24 | 24 | 24 | 24 |
| Polyoxyethylene (2) isostearyl ether | 20 | 20 | 20 | 20 |
| "Merquat" (product of Calgon, 35 wt. % aq. soln) | 8 | 8 | | |
| "Polymer JR400" (product of Union Carbide) | | | 0.5 | |
| "Amodimethicone SM8702C" (product of Dow Corning Toray Silicone) | | | | 2 |
| Sodium sulfite | 0.05 | 0.05 | 0.05 | 0.05 |
| Ascorbic acid | 0.5 | 0.5 | 0.5 | 0.5 |
| Perfume | q.s. | | | |
| Ammonium chloride | Amount to adjust pH to 10 | | | |
| Purified water | Balance | | | |
| Second part | | | | |
| Hydrogen peroxide | 6 | 3 | 3 | 3 |
| Methylparaben | 0.5 | 0.5 | 0.5 | 0.5 |
| Phosphoric acid | Amount to adjust pH to 3.5 | | | |
| Purified water | Balance | | | |

With 1 part by weight of the first part, 1.5 parts by weight of the second part is mixed.

TABLE 4

| | Examples (wt. %) | | | |
|---|---|---|---|---|
| | 15 | 16 | 17 | 18 |
| First part | | | | |
| Compound (1a) | 0.1 | | | |
| Compound (2a) | | 1 | | |
| Compound (3a) | | | 1 | |
| Compound (4a) | 0.1 | | | 1 |
| Tetrasodium ethylenediaminetetraacetate tetrahydrate | | 0.5 | | |
| Trisodium ethylenediaminehydroxyethyltriacetate | | | 2 | |
| Pentasodium diethylenetriaminepentaacetate | | | | 1 |
| Toluene-2,5-diamine | | | 1.9 | |
| p-Aminophenol | | | | 1 |
| Resorcin | 2 | | | |
| p-Amino-o-cresol | | | | 1.1 |
| 2,4-Diaminophenoxyethanol | | | 1.37 | |
| Basic Red 12 | 0.2 | 0.2 | | |
| Basic Red 76 | 0.1 | | 0.2 | |
| HC Red 3 | | 0.1 | | 0.2 |
| Monoethanolamine | 5 | 5 | 5 | 5 |
| Propylene glycol | 8 | 8 | 8 | 8 |
| Polyoxyethylene (20) isostearyl ether | 24 | 24 | 24 | 24 |
| Polyoxyethylene (2) isostearyl ether | 20 | 20 | 20 | 20 |
| "Merquat" (product of Calgon, 35 wt. % aq. soln) | 8 | 8 | | |
| "Polymer JR400" (product of Union Carbide) | | | 0.5 | |
| "Amodimethicone SM8702C" (product of Dow Corning Toray Silicone) | | | | 2 |
| Sodium sulfite | 0.05 | 0.05 | 0.05 | 0.05 |
| Ascorbic acid | 0.5 | 0.5 | 0.5 | 0.5 |
| Perfume | q.s. | | | |
| Ammonium chloride | Amount to adjust pH to 10 | | | |
| Purified water | Balance | | | |
| Second part | | | | |
| Hydrogen peroxide | 6 | 3 | 3 | 3 |
| Methylparaben | 0.5 | 0.5 | 0.5 | 0.5 |
| Phosphoric acid | Amount to adjust pH to 3.5 | | | |
| Purified water | Balance | | | |

With 1 part by weight of the first part, 1.5 parts by weight of the second part is mixed.

After 1 part by weight of the first part was mixed with 1.5 parts by weight of the second part, the mixture was applied to black hair at 30° C. The mixture was allowed to act on the hair for 30 minutes. The hair was then shampooed with an ordinary shampoo and dried. As a result of observation of the color tone of the hair thus dyed, each hair dye composition exhibited good bleaching and dyeing properties.

The invention claimed is:

1. A hair dye composition to be used as a mixture of a first part containing an alkali agent and a second part containing an oxidizing agent, wherein the composition comprises the following components (a) to (c):

(a) a triazacyclononane compound represented by the following formula (1):

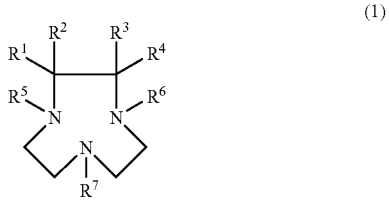

wherein, $R^1$, $R^2$, $R^3$ and $R^4$ each represents a hydrogen atom or a $C_{1-6}$ alkyl group which may be substituted by a hydroxy group, $R^5$, $R^6$ and $R^7$ each represents a hydrogen atom, a $C_{1-6}$ alkyl group which may have a substituent, an aralkyl group which may have a substituent, a heteroarylalkyl group which may have a substituent, an aryl group which may have a substituent, a heteroaryl group which may have a substituent, a $C_{1-6}$ acyl group which may have a substituent or a group represented by the following formula (2):

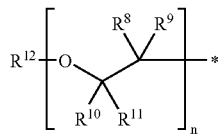

(2)

(in which $R^8$, $R^9$, $R^{10}$, $R^{11}$ and $R^{12}$ each represents a hydrogen atom, a $C_{1-6}$ alkyl group, an aralkyl group or an aryl group, and n stands for 2 to 30), or salt thereof, (b) 0.1 to 12 wt. %, in terms of hydrogen peroxide, of an oxidizing agent, and (c) 0.05 to 10 wt. % of an alkali agent; and the mixture has a pH of from 7.5 to 12.

2. The hair dye composition of claim 1, further comprising ethylenediaminetetraacetic acid, ethylenediaminehydroxyethyltriacetic acid, or diethylenetriaminepentaacetic acid or salt thereof.

* * * * *